(12) United States Patent
Mori et al.

(10) Patent No.: US 7,502,654 B2
(45) Date of Patent: Mar. 10, 2009

(54) ELECTRODE DEVICE HAVING RECESSED PART

(75) Inventors: Kenji Mori, Tsukuba (JP); Hiroyuki Maeda, Tsukuba (JP); Naruhito Higo, Tsukuba (JP); Shuji Sato, Kawasaki (JP); Yasushi Fuchita, Tokyo (JP); Tatsuya Ogawa, Tokyo (JP); Saori Takahashi, Tokyo (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 319 days.

(21) Appl. No.: 10/517,535

(22) PCT Filed: Jun. 11, 2003

(86) PCT No.: PCT/JP03/07406

§ 371 (c)(1),
(2), (4) Date: Sep. 12, 2005

(87) PCT Pub. No.: WO03/105949

PCT Pub. Date: Dec. 24, 2003

(65) Prior Publication Data

US 2006/0206186 A1 Sep. 14, 2006

(30) Foreign Application Priority Data

Jun. 12, 2002 (JP) .............................. 2002-171985

(51) Int. Cl.
*A61N 1/00* (2006.01)
(52) U.S. Cl. ..................................... 607/153
(58) Field of Classification Search .............. 607/152, 607/153; 604/20, 501; 600/387; 200/61.43, 200/512
See application file for complete search history.

(56) References Cited

U.S. PATENT DOCUMENTS

| | | | | |
|---|---|---|---|---|
| 4,021,630 | A | * | 5/1977 | Taylor .................. 200/512 |
| 4,919,648 | A | * | 4/1990 | Sibalis .................. 604/20 |
| 5,125,894 | A | * | 6/1992 | Phipps et al. .......... 604/20 |
| 5,248,295 | A | * | 9/1993 | Jacobsen et al. ....... 604/20 |

(Continued)

FOREIGN PATENT DOCUMENTS

JP  1177814 A1  2/2002

OTHER PUBLICATIONS

Patent Abstracts of Japan, JP 5-132017 A, dated May 28, 1993, and English Abstract thereof.

(Continued)

*Primary Examiner*—George Manuel
(74) *Attorney, Agent, or Firm*—Townsend & Banta

(57) ABSTRACT

The invention provides an electrode device that prevents disconnection of an electrode layer effectively by reducing stress at the time when a recess is formed.

An electrode device (10) has a protrusion (70), which projects upward, in the part of an outward flange section (110*f*), other than a recess (60) formed by molding. The protrusion (70) is arranged so as to surround an outer periphery of the recess (60). When the recess (60) is cold-pressed, the protrusion (70) prevents warp (warp waving along a peripheral direction) in the outward flange section (110*f*) from occurring. Consequently, the protrusion (70) also eases warp of an electrode layer (30) extending on the outward flange section (110*f*) and prevents disconnection of the electrode layer (30).

6 Claims, 2 Drawing Sheets

U.S. PATENT DOCUMENTS

| | | | |
|---|---|---|---|
| 6,629,968 B1 * | 10/2003 | Jain et al. | 604/501 |
| 6,731,987 B1 * | 5/2004 | McAdams et al. | 607/152 |
| 6,915,159 B1 * | 7/2005 | Kuribayashi et al. | 604/20 |
| 2003/0066741 A1 * | 4/2003 | Burgess et al. | 200/61.43 |

OTHER PUBLICATIONS

Patent Abstracts of Japan, JP 11-349786, dated Dec. 21, 1999, and English Abstract thereof.

* cited by examiner

ELECTRODE DEVICE HAVING RECESSED PART

TECHNICAL FIELD

The present invention relates to an electrode device applicable to organisms that is used in a medical field of treatment and diagnosis of diseases, and in particular, to an electrode device having a recess in which a drug or a physiologically active substance is put.

BACKGROUND ART

The iontophoresis (Acta Dermatol venereol, vol. 64, page 93, 1984) and the electroporation (a published Japanese Publication of International Patent Application No. 3-502416, Proc. Acad. Sci. USA, vol. 90, pages 10504 to 10508, 1993) are processing methods of introducing a drug or a physiologically active substance into an organism from a skin or a mucous membrane using electric energy. In addition, there is a method of extracting a diagnosis substance from an organism to observe a condition of the organism using the same principle as those methods (Nature Medicine, vol. 1, pages 1198 to 1201, 1995). In such a method, an electrode device is required in order to apply electric energy. The electrode device generally includes a recess for putting gel of polymer molecules and the like including an electrolyte.

Japanese Patent Laid-Open No. 2000-316991 discloses an idea of making this type of electrode device having a recess disposable as opposed to an external power supply device that is used repeatedly. Japanese Patent Laid-Open No. 2000-316991 proposes a form in which a substrate film including an outward flange section, which surrounds a recess opened upward and a periphery of the opening of the recess, and a lead section, which extends from the outward flange section, and an electrode layer leading to the lead section from a bottom and a sidewall of the recess through the outward flange section on the substrate film are provided and gel containing a drug and the like is arranged on the electrode layer in the recess. The gel or a conductor in the recess is sealed by a cap member covering the recess. In use, the cap member is peeled and brought into contact with an organism. The cap member is adhered to the flange section of the substrate film and seals the recess in a sealed state.

Incidentally, it has been found that, when such an electrode device having a recess is produced in large quantities, there are technical problems as described below. A first problem is prevention of disconnection of an electrode layer. In the electrode layer that extends from the bottom of the recess to cross a step, disconnection tends to occur in the step portion of the recess. It is considered that a main cause of the disconnection is stress (stress caused by a difference between elongation of the substrate film and elongation of the electrode layer involved in the formation) at the time when the recess is molded.

In addition, as another problem, there is prevention of leakage of the gel from the recess and improvement of seal strength of the cap member. In order to bring the cap member into contact with the organism surely, it is necessary to fill the gel in the recess (that is, to the height of the outward flange section). Thus, it is highly likely that leakage of the gel is caused. In turn, the leakage causes decrease in the seal strength of the cap member.

DISCLOSURE OF THE INVENTION

The invention has been devised generally taking into account the above problems that should be solved, and it is basically an object of the invention to provide an electrode device that is adapted to prevent disconnection of an electrode layer effectively by reducing stress at the time when a recess is formed.

In addition, it is another object of the invention to provide an electrode device that can realize prevention of leakage of gel from a recess and improvement of seal strength of a cap member.

Other objects of the invention will be apparent from the following explanation.

In the invention, an outward flange section of a substrate film is deformed so as to project or hollow, and a deformed portion is formed so as to surround a recess on the outward flange. As the deformed portion, it is possible to apply both a projecting form that is convex upward and a hollowing form that is convex downward. In addition, the deformed portion may be single but can also be arranged double or triple. It is possible to form such a deformed portion using molding (cold pressing) of a recessed portion. In a preferred form, the deformed portion is formed continuously on the outward flange section excluding an area where the electrode layer extends.

When the recess is cold-pressed, the deformed portion prevents warp (warp waving along a peripheral direction) in the outward flange section, eases warp in the electrode layer extending on the outward flange, and prevents disconnection of the electrode layer. The deformed portion projecting upward is particularly preferable. When gel containing an electrolyte such as a drug is put in the recess, the deformed portion serves as a seal portion for a cap member for stopping leakage of the gel and covering the recess and can also realize improvement of the seal strength. In this regard, it is advisable to constitute the deformed portion of a form, which is convex upward, so as to be easily crushed to be flat by a seal pressure. As a sectional shape of the deformed portion, it is advisable to adopt an arc, a triangular, or a polygon. In addition, as a dimension of the deformed portion, it is advisable to set a height of a protrusion to 0.5 to 0.01 with respect to a width of 1 of the protrusion serving as the deformed portion. For example, in a range of such a ratio, a width is set to 0.5 mm to 5 mm, and a height is set to 2.5 mm to 50 µm. The height of the protrusion serving as the deformed portion should be set larger than a thickness of a heat seal layer over a surface of the cap member (e.g., 25 to 50 µm) in order to improve the seal strength effectively.

As the substrate film itself, it is possible to apply a member obtained by laminating a plastic film and a metal film extensively like the one described in Japanese Patent Laid-Open No. 2000-316991. In order to deform the electrode device itself to some extent to be adhered a skin when the electrode device is used, it is advisable to make it possible to bend the substrate film with a hand and to keep a bent state. In this regard, as indicated by Japanese Patent Laid-Open No. 11-54855, thicknesses of the plastic film and the metal film should be set to 10 to 200 µm, respectively, and a layer structure should be adopted taking into account a restoration characteristic for returning a bent state of the plastic film to its original state and a shape holding power for holding a bent state of the metal film. As a boundary condition, a thickness of the plastic film is 2 with respect to a thickness of the metal film of 1. Other than this shape holding characteristic, taking into account cost and the like, the thicknesses are preferably 30 to 100 µm. In particular, it is advisable to set the respective thicknesses equivalent at 40 to 80 µm, respectively. As a material for the plastic film, polyethylene terephthalate excellent in electrical insulating properties is preferable. Besides, it is also possible to use polyimide, polyolefin such as polyethylene or polypropylene, or polyester represented by polyethylene naphthalate. On the other hand, as a material for the metal film, aluminum or an alloy of aluminum is preferable. Besides, it is also possible to use copper, tin, silver, gold, lead, or alloys of these metals. A most preferable laminate form of the substrate film is a sandwich form in which upper and lower surfaces of the metal film are sandwiched by plastic films.

The electrode device having the recess is obtained by, after forming an electrode layer on a surface of the base film, in order to avoid thermal destruction of the electrode layer, forming a recess by cold pressing and, then, blanking the laminated material in a predetermined shape. To form the electrode layer on the substrate film, it is preferable to apply printing such as screen printing or gravure printing to the substrate film. As a material for the electrode layer, it is possible to apply various electrode materials. When the electrode layer is formed by printing, it is possible to use, for example, conductive paste ink. In addition, in order to prevent the part of the electrode layer from coming into direct contact with a skin, it is preferable to provide an insulating layer so as to cover at least a part of the electrode layer. It is also possible to form this insulating layer with printing.

BEST MODE FOR CARRYING OUT THE INVENTION

Figure 1:
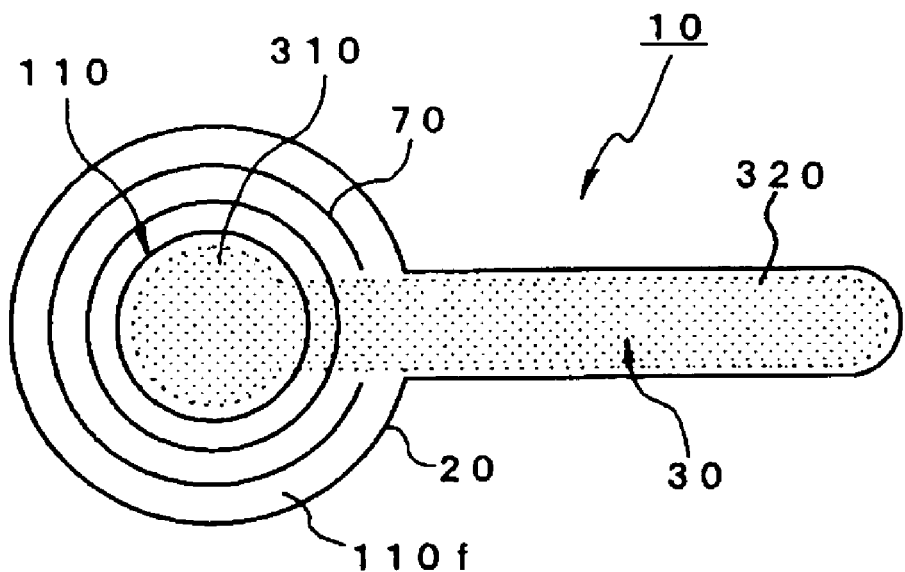
FIG. 1 is a plan view of an embodiment of the invention.
Figure 2:
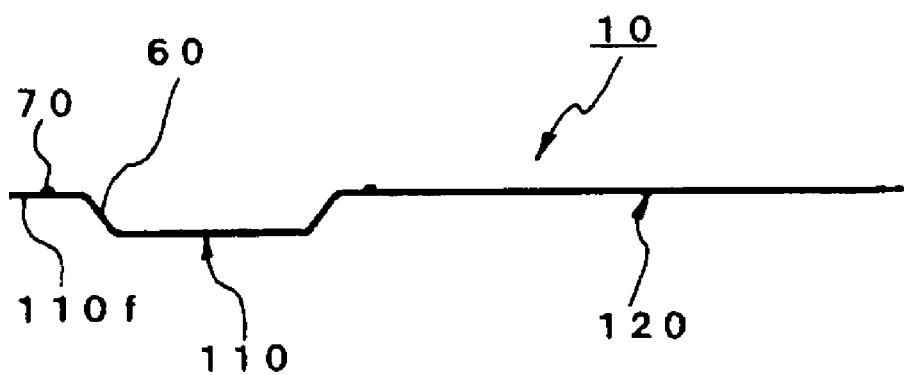
FIG. 2 is a sectional view of the embodiment in FIG. 1.
Figure 3:
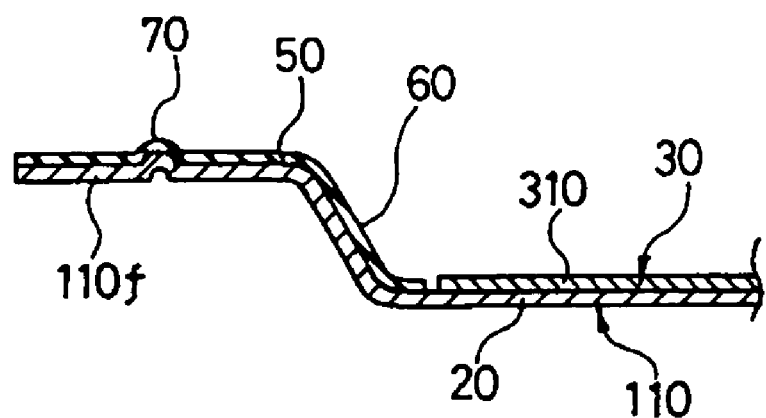
FIG. 3 is a partially enlarged view showing a part of FIG. 2 in enlargement.

An embodiment shown in the figures is an electrode device of an aluminum laminate cup type having a recess. FIG. 1 is a plan view of the electrode device, FIG. 2 is a sectional view of the electrode device, and FIG. 3 shows a part of FIG. 2 in enlargement. In this electrode device 10, an aluminum laminate rolled film obtained by laminating aluminum is used as a material for the substrate film 20. The aluminum laminate rolled film is a laminate film with a layer structure comprising polyethylene terephthalate (38 μm)/aluminum (50 μm)/polyethylene terephthalate (38 μm). First, an electrode layer 30 is formed by applying the screen printing to a surface of this aluminum laminate film using conductive paste ink and, then, drying the conductive paste ink for two minutes at 130° C. As the conductive paste ink, one containing silver, silver chloride, or carbon as a principal component is used. In particular, it is advisable to adopt silver as an electrode component used as an anode and adopt silver chloride containing silver on a cathode side because these are not polarized. The electrode layer 30 includes a circular electrode body 310 with a diameter of about 17 to 18 mm, and an electrode lead section 320 extending linearly from the electrode body 310. A width of the electrode lead section is about 10 mm and a length thereof is about 35 mm.

Moreover, an insulating layer 50 is formed in a part on the substrate film 20 excluding the electrode body 310. The insulating layer 50 has a thickness of, for example, about 10 μm and can be formed by the screen printing using insulating ink. As the insulating ink, here, one comprising 300 parts by weight of polyester resin, 525 parts by weight of cyclohexanon, 175 parts by weight of propylene glycol monomethyl ether acetate, 24 parts by weight of bentonite, and 9 parts by weight of silica is used. After finishing the series of printing work, the cold pressing and the blanking are applied to a laminated material with a structure comprising the substrate film 20/the electrode layer 30/the insulating layer 50 to obtain the electrode device 10 that includes a cup portion 110 having a recess 60 and a lead section 120 extending from the cup portion 110. A depth of the recess 60 of the cup portion 110 is about 2 mm, an inner diameter of the recess 60 is about 25 mm, and an outer diameter of the cup portion 110 is about 40 mm. Therefore, a size of an outward flange section 110f of a periphery of an opening of the recess 60 is 10 to 15 mm.

Figure 4:
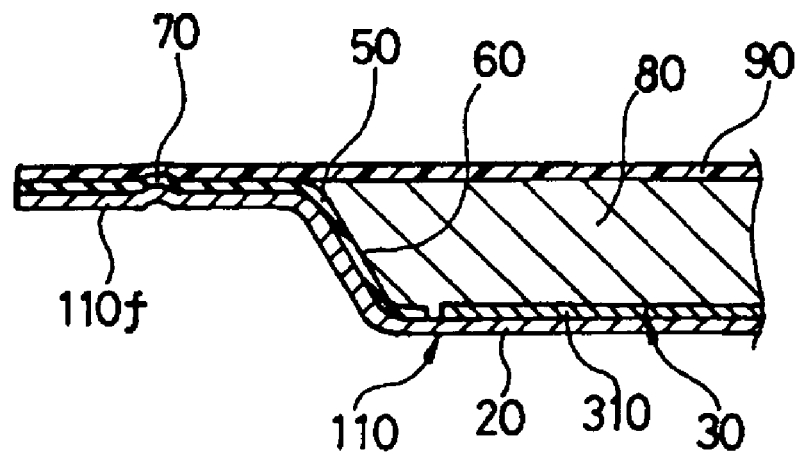
FIG. 4 is a diagram similar to FIG. 3 and including gel and a cap member.

As more clearly indicated by, in particular, FIG. 3, the electrode device 10 having the cut portion 110 includes a protrusion (deformed portion) 70 projecting upward in the part of the outward flange section 110f in addition to the recess 60 formed by molding. The protrusion 70 is molded together with the recess 60 and slightly swells compared with the other parts of the flange section 110f. The protrusion 70 serving as the deformed portion is, for example, a small portion with a width of about 1 mm and a height of about 0.2 mm that may be crushed by a seal pressure at the time of heat seal for a member to be performed later. The protrusion 70 continuously surrounds an outer periphery of the recess 60 excluding the electrode lead 320 of the electrode layer 30. In filling gel 80 in the recess 60, the protrusion 70 can stop the gel that is about to leak out from the recess 60. Therefore, filling work for the gel is facilitated. Moreover, as shown in FIG. 4, in covering the recess 60 filled with the gel 80 using the cap member 90, the protrusion 70 can also improve seal strength of the cap member 90 and the outward flange section 110f.

The cap member 90 is prepared separately from the electrode device 10 having the cup portion 110 and integrated with the cup portion 110 of the electrode device 10 by the heat seal. The cap member 90 has a heat seal layer on a surface of a base layer. For example, it is possible to obtain the cap member 90 by applying an anchor coat agent (a composition comprising 10 parts of Takelac A-536 of Mitsui Takeda Chemicals, Inc., 2 parts of Takenate A-50 of Mitsui Takeda Chemicals, Inc, and 80 parts of methyl acetate) to a surface of polyethylene terephthalate (PET) with a thickness of 50 to 100 μm using a gravure plate, and drying the coat agent to form a coated layer, laminating resin (a composition comprising 90 parts of Acryft CM8011 and 10 parts of Acryft WK402 of Sumitomo Chemical Co., Ltd.) with a thickness of 30 μm is laminated on the coated layer as sealant resin by an extrusion lamination method, and blanking the laminated material in a predetermined size. It is needless to mention that a laminated material comprising the base layer/the coated layer/the sealant layer can be handled in a wound form.

When an experiment was conducted comparing the flange section provided with the protrusion 70 and the flange section not provided with the protrusion 70, warp (wrinkle and sagging) tended to occur in the outward flange section in the case in which the protrusion 70 was not provided. Therefore, it was likely that the insulating layer and the electrode layer warped in a step portion leading to the outer flange section from the recess 60 to cause crack. On the other hand, it was found that, in the flange section provided with the protrusion 70, warp was not caused in the outward flange section 110f, the insulating layer and the electrode layer in the step portion were stable, and the likelihood of crack and disconnection was reduced.

In addition, in the case in which the protrusion 70 was provided, other than the prevention of disconnection, there were an advantage that the filling work for gel was facilitated and an advantage that the seal strength of the cap member 90 was improved. In the case in which the deformed portion is provided in a form of a hollow rather than the form of the protrusion 70, apart from the points of the filling of gel and the seal strength, the same effects as in the case of the protrusion can be obtained for the purpose of the prevention of the disconnection. The hollow around the recess 60 can receive leaking-out gel and prevent the gel from leaking out further to the outside. Consequently, the cap member 90 is heat-sealed further on the outside than the hollow, whereby it is possible to obtain a disconnection prevention effect and an effect that the filling work for gel is facilitated. Therefore, the deformed portion in the outward flange section 110$f$ is formed in a double arrangement of the deformed portion in the inner periphery and the protrusion in the outer periphery. It is also possible to realize improvement of the seal strength of the cap member 90 with the protrusion in the outer periphery.

When the flange section provided with the protrusion 70 of a ring shape as the deformed portion and the flange section not provided with the protrusion 70 were prepared, and an experiment was conducted concerning the seal strength of the cap member 90, results indicated in Tables 1 and 2 shown below were obtained. The seal strength is data according to a T-type peel strength test. In Table 2, values in Table 1 are converted into values of a unit of SI. From these results, the seal strength is large in the flange section marked "present" provided with the protrusion 70 compared with the flange section marked "absent" not provided with the protrusion 70. Moreover, as it is seen from a standard deviation, when the seal strength is large, fluctuation in the seal strength is small. When the seal strength was examined by varying a seal temperature between 180° C. and 240° C., it was impossible to obtain satisfactory adhesion at the seal temperature of 180° C., and it was impossible to seal the cap member 90 because PET, which is a substrate of the cap member 90, was thermally melted at the temperature of 240° C. Therefore, the seal temperature is preferably 190° C. to 230° C. and, in particular, more preferably a temperature with small fluctuation of the seal strength (around 220° C.).

TABLE 1

| Seal temperature | Pro-trusion | Seal strength (g/15 mm) | | | | | | Standard deviation |
|---|---|---|---|---|---|---|---|---|
| | | 1 | 2 | 3 | 4 | 5 | Average | |
| 200° C. | Present | 146 | 166 | 182 | 185 | 195 | 174.8 | 17.15 |
| | Absent | 116 | 140 | 147 | 156 | 170 | 145.8 | 17.96 |
| 220° C. | Present | 168 | 171 | 173 | 174 | 184 | 174.0 | 5.40 |
| | Absent | 145 | 148 | 161 | 167 | 183 | 160.8 | 13.75 |

TABLE 2

| Seal temperature | Pro-trusion | Seal strength (N/15 mm) | | | | | | Standard deviation |
|---|---|---|---|---|---|---|---|---|
| | | 1 | 2 | 3 | 4 | 5 | Average | |
| 200° C. | Present | 1.43 | 1.63 | 1.78 | 1.81 | 1.91 | 1.71 | 0.17 |
| | Absent | 1.14 | 1.37 | 1.44 | 1.53 | 1.67 | 1.43 | 0.18 |
| 220° C. | Present | 1.65 | 1.68 | 1.70 | 1.71 | 1.80 | 1.71 | 0.05 |
| | Absent | 1.42 | 1.45 | 1.58 | 1.64 | 1.79 | 1.58 | 0.13 |

INDUSTRIAL APPLICABILITY

According to the invention, in an electrode device applicable to organisms that is used in a medical field of treatment and diagnosis for diseases, it is possible to prevent disconnection of an electrode layer effectively and realize prevention of leakage of gel from a recess and improvement of seal strength of a cap member.

The invention claimed is:

1. An electrode device, comprising:
   (a) a substrate film including:
      (i) a cup portion having a recess, a bottom disposed adjacent one end of the recess, and a periphery disposed adjacent an end of the recess opposite the bottom, said cup portion opened upward;
      (ii) an outward flange section surrounding the periphery of the cup portion, and disposed in communication therewith, and
      (iii) a deformed portion formed in the outward flange section, so as to surround the periphery of the cup portion, said deformed portion operable to cause the outward flange section of the substrate film to project or hollow; and
   (b) an electrode layer printed on the substrate film, including:
      (i) an electrode body arranged on the bottom of the cup portion; and
      (ii) an electrode lead section extending from the bottom of the cup portion, up the recess, and over the outward flange section on the substrate film.

2. The electrode device according to claim 1, wherein the substrate film further comprises a laminated member obtained by laminating a plastic film and a metal film, said laminated member capable of being easily bent with a hand, and being held in a bent state.

3. The electrode device according to claim 1, further comprising a cap member disposed adjacent to and in communication with the outward flange section, so as to cover the cup portion, wherein deformed portion comprises a projection operable to seal the cap member covering the recess.

4. The electrode device according to claim 3, further comprising gel containing an electrolyte disposed in the cup portion so as to be retained therein by the recess, wherein the projection of the deformed portion prevents leakage of the gel when the gel is put in the recess.

5. The electrode device according to claim 1, wherein the deformed portion is formed using molding of the recess.

6. The electrode device according to claim 1, wherein the deformed portion is continuously formed on the outward flange excluding a region where the electrode layer extends.

* * * * *